(12) United States Patent
Bacher et al.

(10) Patent No.: US 8,926,608 B2
(45) Date of Patent: Jan. 6, 2015

(54) BIPOLAR MEDICAL INSTRUMENT

(75) Inventors: Uwe Bacher, Tuttlingen (DE); Martin Blocher, Tuttlingen (DE); Daniel Weinmann, Seitingen-Oberflacht (DE)

(73) Assignee: Karl Storz GmbH & Co. KG (DE)

( * ) Notice: Subject to any disclaimer, the term of this patent is extended or adjusted under 35 U.S.C. 154(b) by 1466 days.

(21) Appl. No.: 12/237,952

(22) Filed: Sep. 25, 2008

(65) Prior Publication Data
US 2009/0082768 A1 Mar. 26, 2009

(30) Foreign Application Priority Data

Sep. 25, 2007 (DE) .......................... 10 2007 047 243

(51) Int. Cl.
*A61B 18/14* (2006.01)

(52) U.S. Cl.
CPC .................................. *A61B 18/1445* (2013.01)
USPC ............................................................. 606/51

(58) Field of Classification Search
CPC ........... A61B 18/1442; A61B 18/1445; A61B 18/1447; A61B 2018/00196; A61B 2018/00589; A61B 2018/00601; A61B 2018/00607; A61B 2018/00126; A61B 2017/2936
USPC ......................................... 606/48, 50, 51, 52
See application file for complete search history.

(56) References Cited

U.S. PATENT DOCUMENTS

| | | | |
|---|---|---|---|
| 5,391,166 A * | 2/1995 | Eggers | 606/48 |
| 5,496,317 A | 3/1996 | Goble et al. | |
| 5,697,949 A * | 12/1997 | Giurtino et al. | 606/205 |
| 5,853,412 A * | 12/1998 | Mayenberger | 606/51 |
| 6,063,086 A | 5/2000 | Benecke et al. | |
| 6,334,860 B1 | 1/2002 | Dorn | |
| 6,669,696 B2 | 12/2003 | Bacher et al. | |
| 2002/0128649 A1* | 9/2002 | Bacher et al. | 606/46 |
| 2003/0181910 A1* | 9/2003 | Dycus et al. | 606/51 |
| 2005/0222611 A1* | 10/2005 | Weitkamp | 606/205 |
| 2006/0173452 A1* | 8/2006 | Buysse et al. | 606/50 |

FOREIGN PATENT DOCUMENTS

| | | |
|---|---|---|
| DE | 19608716 C1 | 4/1997 |
| DE | 29821617 U1 | 1/1999 |
| DE | 19858512 C1 | 5/2000 |
| DE | 19940689 A1 | 4/2001 |

(Continued)

OTHER PUBLICATIONS

European Search Report; EP 08 16 4841; Jan. 9, 2009; 1 page.

(Continued)

*Primary Examiner* — Michael Peffley
*Assistant Examiner* — Thomas Giuliani
(74) *Attorney, Agent, or Firm* — St. Onge Steward Johnston & Reens LLC

(57) ABSTRACT

A bipolar medical instrument has a shaft and two jaw parts arranged at the distal end thereof. An axially movable force transmission element is disposed with the shaft and is surrounded by an isolating element. The isolating element is connected to at least one of the two jaw parts in an articulated manner. The two jaw parts are electrically isolated from one another and each provides an electrode to which high frequency current can be applied. A first electrical supply line is formed along the shaft via an electrically conductive first contact element to one of the two jaw parts. A second electrical supply line is formed along the axially movable force transmission element via an electrically conductive second contact element to the other of the two jaw parts. The first contact element is fixed at the isolating element surrounding the distal end area of the force transmission element.

12 Claims, 5 Drawing Sheets

(56) References Cited

FOREIGN PATENT DOCUMENTS

| | | |
|---|---|---|
| DE | 20118302 U1 | 1/2002 |
| DE | 69432937 T2 | 5/2004 |
| DE | 102004015667 B3 | 1/2006 |
| DE | 60113269 T2 | 6/2006 |
| DE | 60307645 T2 | 2/2007 |
| DE | 60307465 T2 | 8/2007 |
| WO | 9408524 A1 | 4/1994 |

OTHER PUBLICATIONS

European Office Action; Application No. 08 164 841.2-2305; Issued: Mar. 3, 2010; English Translation Included; 5 pages.

\* cited by examiner

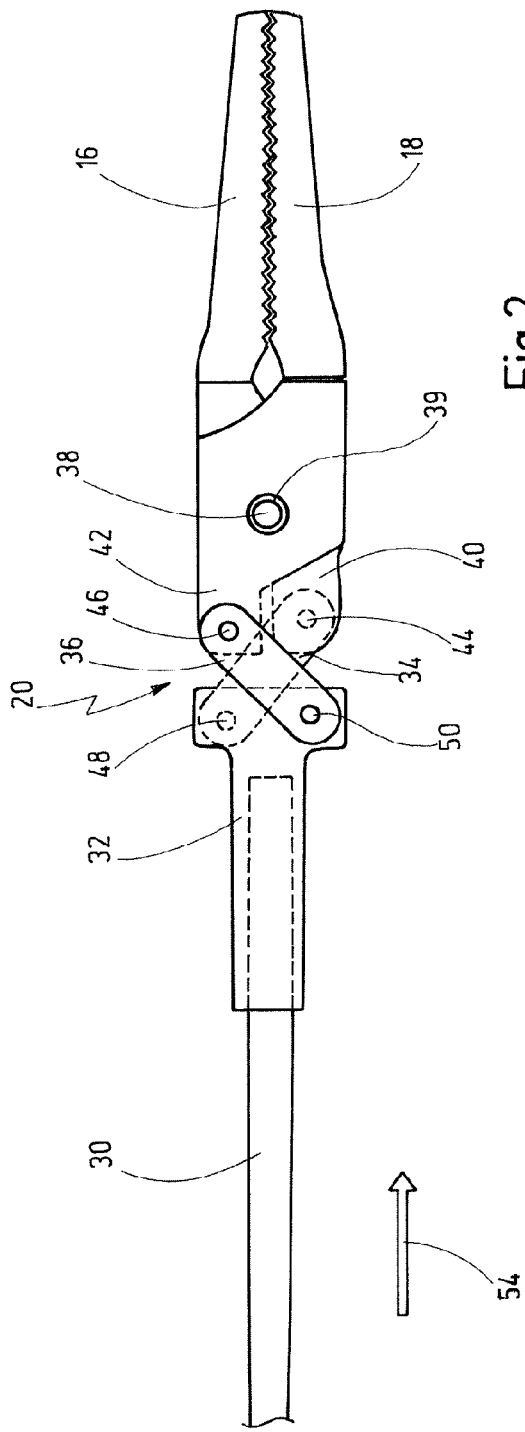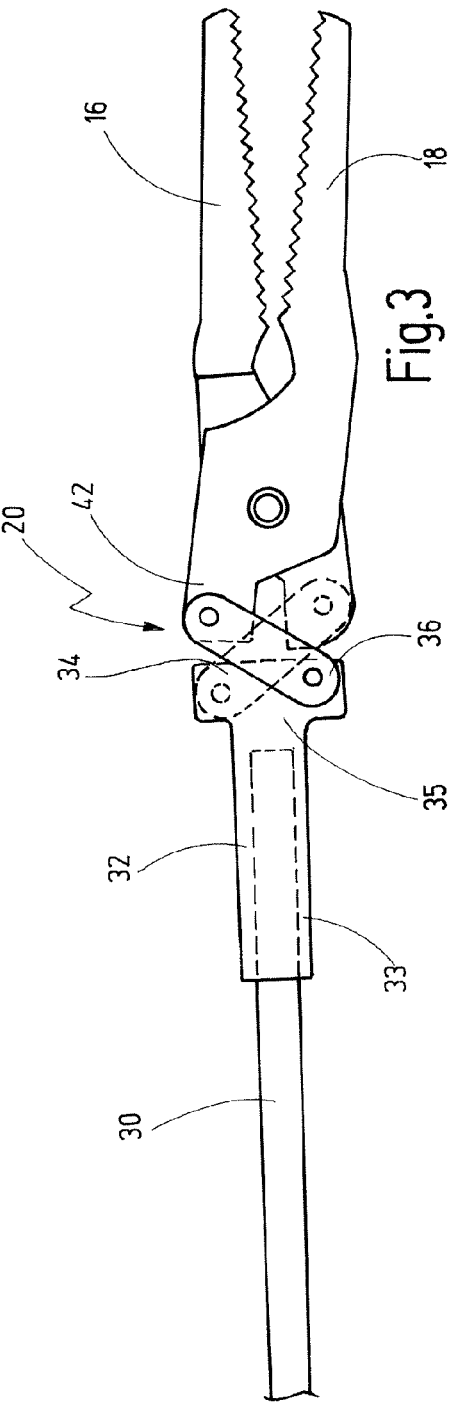

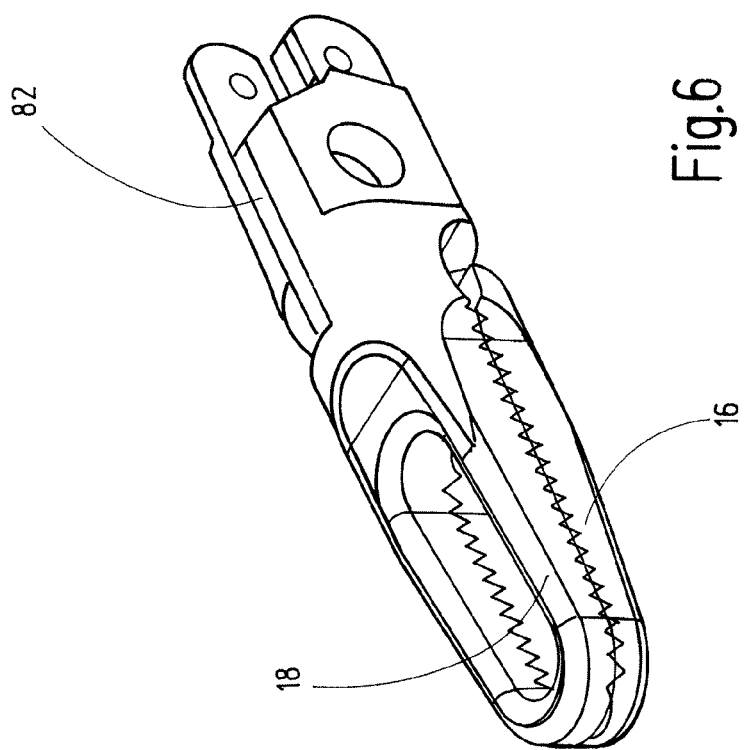

BIPOLAR MEDICAL INSTRUMENT

BACKGROUND OF THE INVENTION

The invention relates to a bipolar medical instrument.

Bipolar medical instruments are used to thermally cut, to coagulate or to cut and to coagulate tissue in a human or animal body under the influence of bipolar high-frequency current.

Bipolar instruments usually have a tubular shaft at whose distal end two jaw parts which are connected to one another in an articulated manner are arranged and can move relative to one another. A force transmission element which can move axially is arranged in the tubular shaft and is connected such that force can transmitted from a handle arranged at a proximal end to at least one jaw part, specifically the moving jaw part arranged at the distal end of the shaft. The jaw parts can be opened and closed by operation of the handle. The jaw parts each form an electrode, to which high-frequency current can be applied and which is of different polarity. Each jaw part has a separate associated electrical power supply line, which is in each case connected to one pole of the high-frequency voltage source. In most cases, the force transmission element acts as an electrically conductive connection to the moving jaw part while, in contrast, the tubular shaft acts as an electrically conductive connection to the other jaw part, irrespective of whether this is a moving or a stationary jaw part.

In such bipolar instruments it is necessary to provide not only adequate electrical insulation between the two electrical power supply lines, but in particular between the two jaw parts in the area of their articulation points, in order to avoid shorts via leakage current during use.

The electrical isolation of the two jaw parts from one another in the area of the joint has the problem that, particularly in the case of thin instruments, these isolating elements are very small and their mechanical strength is remarkably reduced. Since a high-frequency voltage in the order of magnitude of 2.5 kV is normally applied to jaw parts, this means, that, if the isolating elements are physically small, a voltage flashover will take place or a creepage current will be formed via the isolating element to the closest conductive component, which leads to a short.

In use, the jaw parts come into contact with electrically conductive liquids, in particular with body fluids, which can result in creepage currents via the isolating elements, thus leading to shorts. Arcs which damage the isolator can thus be formed.

US 2006/0259036 A1 discloses to design a electrically conductive first contact element for contacting the shaft and one of two jaw parts as an outer nose portion. A distal end of the nose portion is connected to one of the two jaw parts via a stake. The part which is connected with the shaft has the shape of a half pipe. A second contact element provides the electrical conductive connection between the rod-like force transmission element and the second jaw part. The second contact element is again designed as a nose portion connected at its distal end with the second jaw part. The second conductive element has a half pipe section too for connecting this second contact element with the rod-like force transmission element. Half pipe shaped insulators are disposed between the half pipe parts of the electrically conductive contact elements to insulate against the shaft and rod-like force transmission element, respectively.

When mounted, the two half pipe sections of the two contact elements are arranged close together. During use and in contact with electrically conductive liquids like body liquids, leakage currents can result between these two contact elements of different polarity.

It is therefore object of the present invention to develop a bipolar medical instrument such that the jaw parts are isolated reliably in the long term in the area of the joint, and such that this ensures that forces are transmitted in a mechanically robust form in the long term.

SUMMARY OF THE INVENTION

According to the invention, this object is achieved by a bipolar medical instrument comprising a shaft having a distal end, two jaw parts arranged at said distal end, an axially movable force transmission element disposed within said shaft, a distal end area of said force transmission element being surrounded by an isolated element formed of an insulating material, said isolating element being connected to at least one of said two jaw parts in an articulated manner, said two jaw parts being electrically isolated from one another and each providing an electrode to which high-frequency current can be applied of a different polarity, a first electrical supply line is formed along said shaft, via an electrically conductive first contact element to one of said two jaw parts and a second electrical supply line is formed along said axially movable force transmission element via an electrically conductive second contact element to the other one of said two jaw parts, wherein said first contact element being fixed at said isolating element surrounding said distal end area of said force transmission element.

An advantage is that the first contact element which provides the current flow from the tubular shaft to the associated jaw parts is electrically isolated by the isolating element from the force transmission element. This does not only contribute to save electrical isolation between the two current paths, but the isolating element also acts as a mechanical support or mount for this first contact element. Due to fixing the first contact element at the isolating element surrounding the force transmission element, an exact positioning is given. This allows to design the second contact element very slender, sufficient to guide the current from the shaft to the respective jaw part. The force transmission occurs via the isolating element, i.e. the axial movements of the force transmission element are transferred into an axial movement of the first contact element fixed thereon.

The first contact element is therefore not part of the force transmission part but is fixed to said element transmitting the force of the force transmission element to the jaw parts. Since this isolating element to which the first contact element is fixed is made of an insulating material, a safe isolation is given between this first contact element and the force transmission element which is of the other polarity.

The fact that the first contact element can be designed very slender, since it is not part of the force transmission path to transmit the force to the jaw parts, the distance between this first contact element and the other second contact element can be made relatively great. This relatively great distance prevents leakage currents dramatically. This further allows to design a very slender shaft of bipolar medical instruments.

Due to the articulated connection between at least one of the two jaw parts with the isolating element surrounding the distal end section of the conductive force transmission element, the force can be transmitted via this isolating element and not via a contact element.

The design allows to fix the first contact element which electrically connects the outer shaft and one of the two jaw parts at the insulating element covering the force transmission element which provides the counterpole to the outer shaft. The first contact element can be fixed at this isolating element at a place which is as far away as possible from the second contact element which contacts the force transmission element and the other jaw part. Therefore, there are different fixation points available for fixing the first contact element at this isolating element but it still performs its function, i.e. to contact the outer shaft with one of the two jaw parts.

In a further design of the invention, the second contact element is arranged circumferentially offset with respect to said first contact element.

This measure has the advantage that the second contact element provides the current flow from the force transmission element to the associated jaw part which can be arranged as far away from the first contact element in order to preclude voltage flashovers.

In a further design of the invention the second contact element is connected via a contact to said force transmission element, said contact being at least one pin passing through a sleeve section of said isolating element. Two pins can preferably be provided.

This measure has the advantage that the pins do not only ensure a mechanically firm binding and thus fixing of the position of this second contact element, but that the two pins deliberately create break-through points in the isolating element in order to pass current from the conductive force transmission element which is held therein via the second contact element to the corresponding jaw part. The position of the pins can then be chosen such that this contact point is as far away as possible from the contact or fixing point of the first contact element which provides the current flow from the tubular shaft to the other jaw part. This again creates breakage or leakage paths of maximum length.

In a further design of the invention, at least one of said two jaw parts is provided with an insulation on a side which faces the other one of said two jaw parts.

This measure has the advantage that the two jaw parts are isolated from one another over a large area by this coating. The two jaw parts may themselves be metallic and therefore be mechanically robust, even in the articulation area, in such a way that the forces during opening and closing of the jaw parts can be transmitted by mechanically robust parts.

In a further design of the invention, said isolating element surrounding said distal end area of said force transmission element is connected to said two jaw parts in an articulated manner.

This measure has the advantage that the isolating element can be used to transmit force to both jaw parts. The articulated connection may comprise metallic parts which are sufficiently robust to transmit the force, for example via a toggle-lever mechanism, while nevertheless not only ensuring adequate isolation in this area in the direction of the conductive force transmission element but also isolation between the two articulated connections. This particularly impressively indicates the suitability of the isolating element for carrying out the dual function of mechanical stability and isolation purposes.

It is of great advantage that at least one of said two jaw parts is provided with an insulation on a side facing the other one of said two jaw parts at least in an area where said jaw parts are connected to said isolating element in an articulated manner.

In a further design of the invention, said two jaw parts are connected to one another via a hinge pivot, said hinge pivot being surrounded by an electrically insulating material.

The hinge pivot via which the two jaw parts are connected in an articulated manner may be metallic, although it must be then surrounded by an insulating sheath at least in an area of a bearing.

It is of great advantage to provide the isolating element surrounding the distal end of said force transmission element with a sleeve section.

In particular with the thin and long shafts it is possible to design this sleeve section correspondingly long. This long dimension allows to make the fixation points of the first and the second contact element as far away as possible to avoid the creation of leakage currents.

In a further design of the invention, the isolating element has a T-section at which at least one of said two parts is mounted in an articulated manner.

This measure has the advantage that the T-section offers mechanical articulation points for the articulated connection to the jaw parts or to a joint connected between them, for example a toggle-lever mechanism even with a slim line design. A mechanically robust articulated connection can be provided in this T-shaped section while at the same time are again created relatively large separations between the components which are intrinsically conductive and are fitted in an articulated manner in order to avoid voltage flashovers in this region. This can be achieved by each of the articulation points of the jaw parts being located at outer opposite ends of the T-section. Advantageously, the insulating materials comprise a ceramic material, preferably a ceramic material which is very hard and not very brittle.

This has the advantage that the electrically isolating elements made from this material can be particularly highly mechanically robust, thus ensuring the whole function that is to save force transmission on the one hand and isolation on the other hand in the long term.

Further advantages will become evident from the following description in conjunction with the attached drawings.

It is self-evident that the features which have been mentioned above and those which are still to be explained in the following text can be used not only in the respectively stated combinations but also in other combinations or on their own without departing from the scope of the present invention.

BRIEF DESCRIPTION OF THE DRAWINGS

Exemplary embodiments of the invention are illustrated in the drawing and will be described in more detail in the following text with reference to the drawing, in which:

FIG. 2 shows a side view of a part of the distal end of the instrument, with the mechanical force transmission for opening and closing the jaw parts being illustrated, and with the jaw parts being shown in the closed state;

FIG. 3 shows an illustration comparable to FIG. 2, with the jaw parts open;

FIG. 6 shows an enlarged perspective view of the two jaw parts.

DETAILED DESCRIPTION OF A PREFERRED EMBODIMENT

Figure 1:
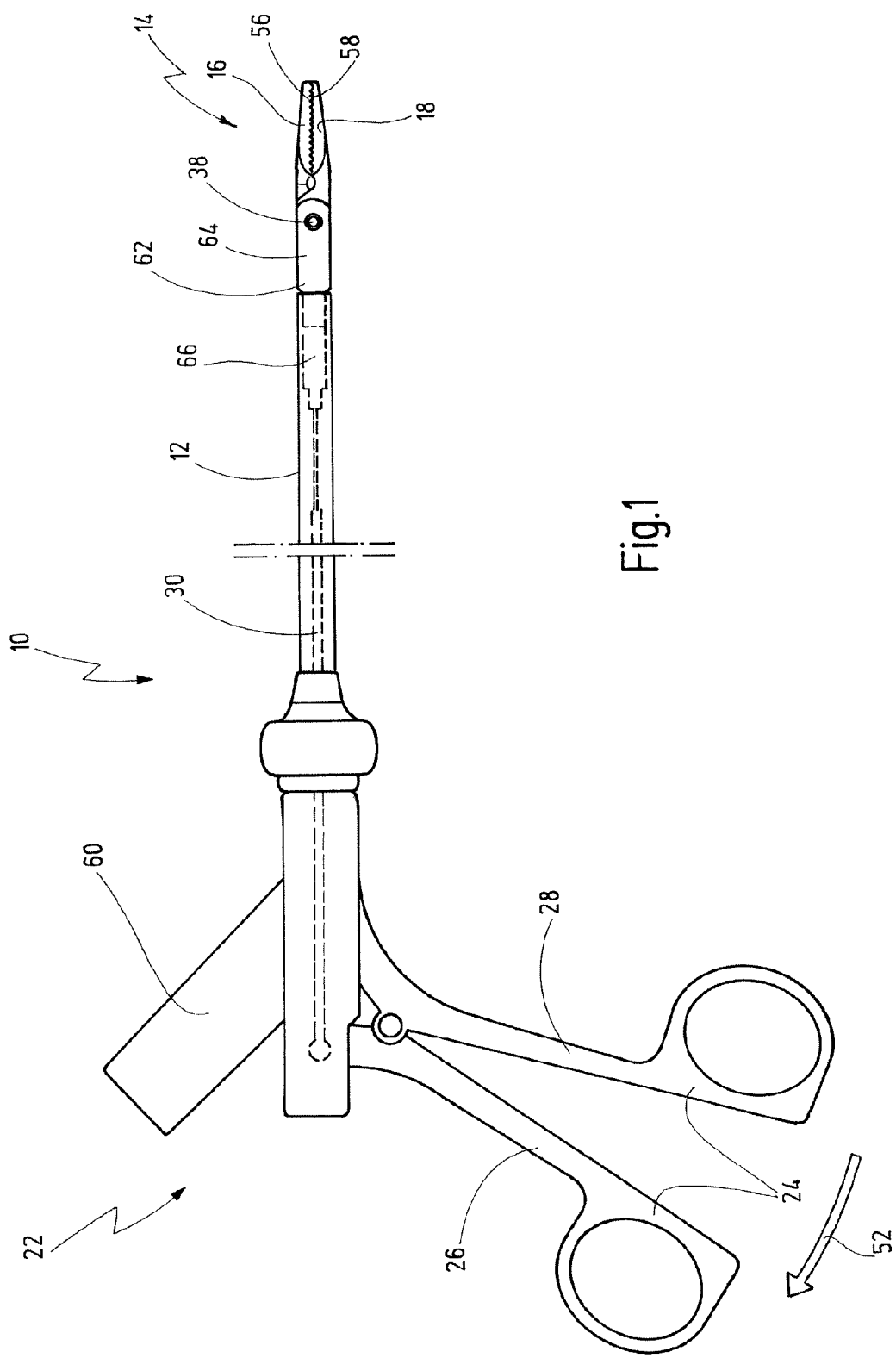
FIG. 1 shows a side view of a bipolar medical instrument according to the invention.

A bipolar medical instrument as illustrated in FIG. 1 is annotated with the reference number 10 in its totality. The instrument 10 is used for minimal-invasive surgical interventions for the treatment of tissue in human or animal bodies, for preparation by means of high-frequency current.

The exemplary embodiment of the instrument 10 illustrated in FIG. 1 is a gripping instrument or gripping tongs.

The instrument 10 has an elongated tubular shaft 12. The tubular shaft 12 is formed from an electrically conductive material, preferably from metal.

Two jaw parts 16, 18 are arranged at a distal end 14 of the tubular shaft 12. The jaw parts 16, 18 are connected to one another via an articulation pivot 38 and can move relative to one another, as will also be described later in conjunction with FIGS. 2 and 3.

A housing 62 is provided at the distal end area of the instrument 10. A distal fork-head-like area 64 of the housing 62 is formed from an electrically insulating material, while, in contrast, a proximal-side area 66 of the housing 62 is formed from an electrically conductive material. This proximal-side area 66 is used for the electrically conductive connection to the tubular shaft 12 and for this purpose is inserted into it. The jaw parts 16 and 18 are connected to the fork-head-like area 64 via the articulation pivot 38.

Furthermore, at its proximal end, the instrument 10 has a handle 24. The handle 24 in this exemplary embodiment comprises two handle parts 26 and 28, with the handle part 26 being moving and the handle part 28 being stationary.

A force transmission element 30 extends in the tubular shaft 12 between the moving handle part 26 and the jaw parts 16 and 18 and, in this exemplary embodiment, is in the form of a push and pull rod. The force transmission element 30 is designed such that it can move axially in the tubular shaft 12.

The force transmission element 30, which is formed from an electrically conductive material, is surrounded at the distal end by an isolating element 32 like a cap, as can be seen in particular from the illustration in FIGS. 2 and 3.

The isolating element 32 is formed from an electrically insulating material, in particular a ceramic material or a ceramically surrounding material, and is connected to the two jaw parts 16, 18 in an articulated manner. A joint 20 is in the form of a toggle-lever arrangement and is used for control and movement of the jaw parts 16 and 18 by means of the force transmission element 30.

The two jaw parts 16 and 18 are in the form of levers which can pivot about the hinge pivot 38. A proximal section 40, 42 of each jaw part 16, 18 is connected in an articulated manner to a respective joint lug 34, 36 by means of a respective rivet 44, 46, as can be seen from the illustration in FIGS. 2 and 3. The joint lugs 34, 36 are connected in an articulated manner at their other end, by means of a respective rivet 48, 50, to a distal end of the isolating element 32. The pivot 38, the joint lugs 34, 36 and the rivets 44, 46, 48 and 50 are formed from metallically conductive material, preferably from metal.

In the view shown in FIGS. 2 and 3, the joint lug 36 is articulated at the "upper" end of the isolating element while, in contrast, the joint lug 34 is articulated diametrically opposite at the "lower" end.

The isolating element 32 is in the form of a T-piece 35. The rivet 50, which is riveted to the T-piece 35 via the "upper" joint lug 36, is located at the opposite end of the cross-bar of the T-piece 35, on which the rivet 48 is located, and via which the "lower" joint lug 34 is riveted.

The joint lugs 34 and 36 cross one another, but are at a distance from one another. The articulation points of the rivets 48 and 50 are at a distance from one another and ensure electrical isolation between these components. This allows the joint lugs 34 and 36 to be formed from metal, and thus to be mechanically robust, in order to transmit the forces for opening and closing the jaw parts 16 and 18. The "upper" joint lug 36 is connected to the "upper" jaw part 18 while, in contrast, the "lower" joint lug 34 is connected to the "lower" jaw part 16.

Figure 5:
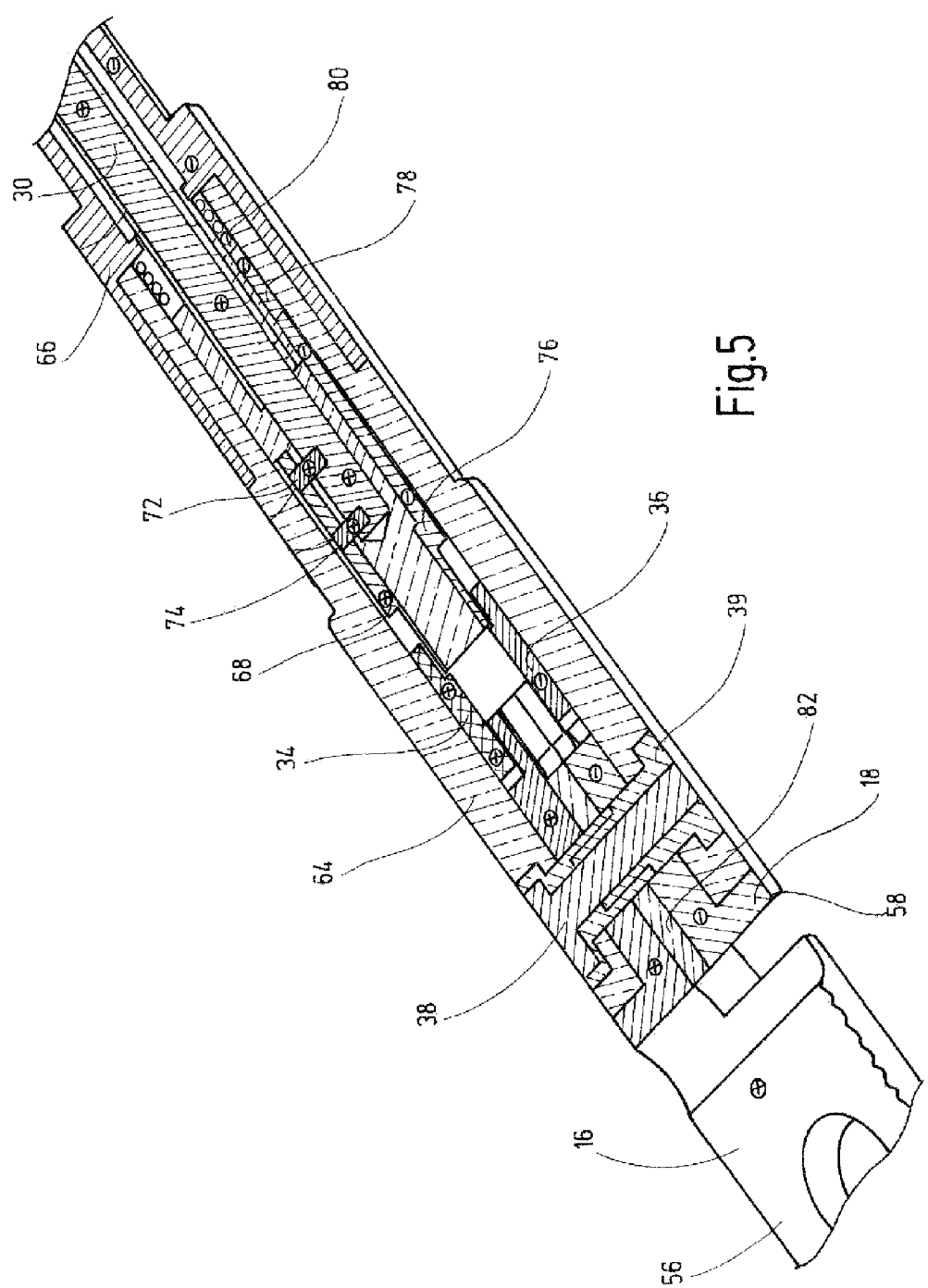
FIG. 5 shows a longitudinal section, which has been somewhat enlarged in places and has been rotated through 90° about the centre axis in comparison to the illustration shown in FIG. 4, of the distal end area of the instrument from FIG. 1.

The hinge pivot 38 which connects the two jaw parts 16 and 18 to one another in an articulated manner and such that they can pivot about it, is surrounded by a two-part plug sleeve 39 composed of insulating material (see FIG. 5).

This creates the electrical isolation between the jaw parts 16 and 18 around their hinge pivot 38. The hinge pivot 38 itself is produced from a metallic material.

The particular configuration of the isolating element 32 makes it possible to keep the different polarities of the electrical power supply for the jaw parts 16 and 18 as far as possible away from one another.

For additional isolation, at least one of the surfaces of the jaw parts 16 and 18 which are opposite one another in the articulation area is provided with an insulating coating. In the illustrated exemplary embodiment, the jaw part 18 is provided with an insulating coating 82 (see FIG. 6).

In order to open the jaw parts 16, 18, the moving handle part 26 of the handle 24 is pivoted in the direction which is indicated by an arrow 52 in FIG. 1. The moving handle part 26 is connected such that force can be transmitted to a proximal end of the force transmission element 30, for example by means of a ball and socket joint, as is known per se. A connection such as this which can transmit force converts a pivoting connection of the handle part 26 to a linear displacement movement of the force transmission element 30, and therefore also of the isolating element 32 (see the arrow 54 in FIG. 2). This displacement movement results in a movement of the joint lugs 34 and 36, which are respectively connected to one of the jaw parts 16 and 18 in an articulated manner. The movement of the joint lugs 34 and 36 results in pivoting of the jaw parts 16 and 18 about their articulation pivots 38, as a result of which the jaw parts 16, 18 are moved to a spread-open state. This situation is illustrated in FIG. 3.

An opposite displacement movement then results in the jaw parts 16 and 18 being closed.

Figure 4:
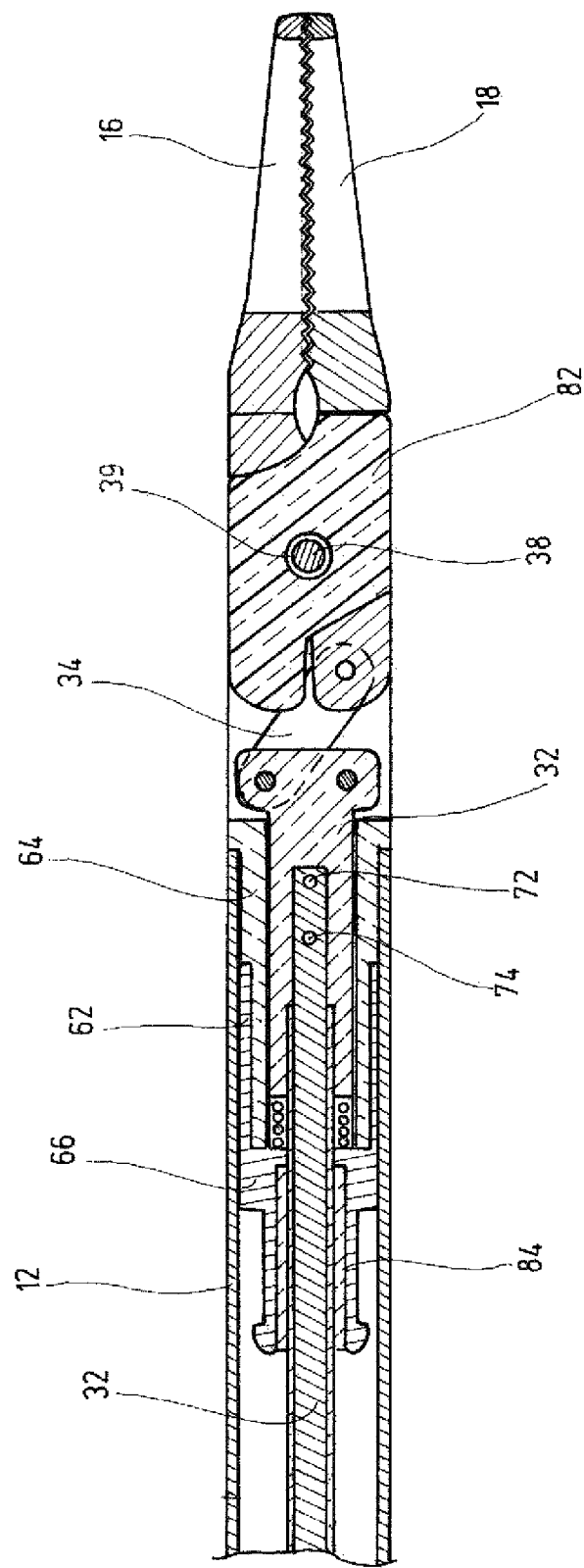
FIG. 4 shows a central longitudinal section of the distal end area of the instrument according to the invention from FIG. 1.

The electrical power supply for the two jaw parts 16 and 18 will be described in more detail in conjunction with FIGS. 4 and 5.

The jaw parts 16 and 18, which in this exemplary embodiment are produced entirely from an electrically conductive material, preferably from metal, form two electrodes 56, 58 of different polarity to which current can be applied. One electrode 56 is connected during operation to one pole of a high-frequency voltage source while, in contrast, the electrode 58 is connected to the other pole of the high-frequency voltage source.

In order to supply current to the jaw parts 16 and 18, the instrument 10 has an obliquely positioned plug connection 60 at the proximal end 22, via which the instrument 10 can be connected to an external high-frequency voltage source, which is not illustrated here.

The force transmission element 30 is used as an electrically conductive connection for the first jaw part 16, while, in contrast, the tubular shaft 12 is used as an electrically conductive connection for the second jaw part 18, as will be described in more detail in the following text.

An electrically conductive second strip-shaped contact element 68 is fixed on an outer face to the isolating element 32 and is conductively connected to the force transmission element 30 via two contact pins 72, 74 which project transversely through a sleeve section 33 of the isolating element 32.

At the distal end, the second contact element 68 is conductively connected to the joint lug 34 of the jaw part 16, as can be seen in particular from the illustration in FIG. 5.

Current therefore flows between the force transmission element 30 and the first jaw part 16 via the second contact element 68 and the joint lug 34. This current flow is indicated by positive signs in FIG. 5, in order to assist understanding.

As has already been explained above, the outer tubular shaft 12 acts as an electrically conductive connection for the second jaw part 18. The current flow is passed from the tubular shaft 12 to the proximal-end area 66 of the housing 62, which is surrounded by the tubular shaft 12 and is conductively connected to the tubular shaft 12 (see FIG. 1).

The first contact element 76 is arranged circumferentially offset with respect to the already described second contact element 68, preferably being arranged through 180°, that is to say diametrically opposite, and is electrically isolated from it by the isolating element 32.

The first contact element 76 is conductively connected via a contact 78 to the proximal-end area 66 of the housing 62. The first contact element 76 is fixed to the isolating element 32, for example via an adhesive or via mechanical anchoring points. The first contact element 76 follows the axial movements of the force transmission element 30. The contact 78 is in the form of a spring-loaded contact 80 in order to ensure effective contact between the housing 62 and the tubular shaft 12 during such movements. The current flow is transmitted from the contact element 76 to the joint lug 36, and then to the second jaw part 18. The first contact element 76 can be designed as a slim long metal strip. It also can be designed as a wire.

The current flow between the tubular shaft 12 and the jaw part 18 therefore passes via the proximal-end area 66 of the housing 62, the spring-loaded contact 80, the first contact element 76 and the joint lug 36. The current flow is indicated by negative signs in FIG. 5.

The force transmission element 30, which is arranged in the tubular shaft 12, and is in the form of a push and pull rod is surrounded by a sheath 84 composed of non-conductive material, for isolation from the tubular shaft 12.

What is claimed, is:

1. A bipolar medical instrument comprising a tubular shaft, further comprising two jaw parts which are arranged such that they can move relative to one another at a distal end of said tubular shaft, with said jaw parts each forming an electrode, to which high frequency current can be applied, of different polarity, wherein each jaw part has an associated separate electrical power supply line, one power supply line supplies current via an electrically conductive tubular shaft to one jaw part, wherein said electrically conductive tubular shaft itself conducts current, and another power supply line supplies current via an axially moving electrically conductive force transmission element to another of the two jaw parts, wherein said electrically conductive force transmission element itself conducts current, said force transmission element being connected to at least one jaw part in a manner that force can be transmitted to said at least one jaw part, and wherein the jaw parts are electrically isolated from one another, and wherein a distal end area of the force transmission element is surrounded by a cap-like or sleeve-like isolating element which is made from an electrically insulating material and which is mounted on the force transmission element, and wherein said isolating element is connected to at least one jaw part in an articulated manner, and wherein an electrically conductive first contact member is provided, by means of which a current flow can be provided from said tubular shaft to one of said jaw parts, and wherein said first contact member is fixed to said isolating element.

2. The bipolar medical instrument of claim 1, further comprising a second contact member, which provides a current flow from the force transmission element to the other jaw part, and which is arranged circumferentially offset with respect to said first contact member.

3. The bipolar medical instrument of claim 2, wherein said second contact member is connected via a contact to said force transmission element, said contact being at least one pin passing through a sleeve section of said isolating element.

4. The bipolar medical instrument of claim 1, wherein at least one of said two jaw parts is provided with an insulation on a side which faces the other one of said two jaw parts.

5. The bipolar medical instrument of claim 4, wherein said insulation is made of a material selected from the group consisting of a ceramic material and a ceramic material which is very hard and not very brittle.

6. The bipolar medical instrument of claim 1, wherein said isolating element surrounding said distal end area of said force transmission element is connected to said two jaw parts in an articulated manner.

7. The bipolar medical instrument of claim 6, wherein at least one of said two jaw parts is provided with an insulation on a side facing the other one of said two jaw parts at least in an area said jaw parts are connected to said isolating element in an articulated manner.

8. The bipolar medical instrument of claim 1, wherein said two jaw parts are connected to one another via a hinge pivot, said hinge pivot being surrounded by an electrically insulating material.

9. The bipolar instrument of claim 8, wherein said electrically insulating material surrounding said hinge pivot is selected from the group consisting of a ceramic material and a ceramic material which is very hard and not very brittle.

10. The bipolar medical instrument of claim 1, wherein said isolating element surrounding said distal end area of said force transmission element has a sleeve section which is mounted on said distal end area of said force transmission element.

11. The bipolar medical instrument of claim 1, wherein said isolating element surrounding said distal end area of said force transmission element has a T-section at which at least one of said two jaw parts is mounted in an articulated manner.

12. The bipolar medical instrument of claim 1, wherein said insulating material is selected from the group consisting of a ceramic material and a ceramic material which is very hard and not very brittle.

* * * * *